United States Patent [19]

Takaya et al.

[11] 4,242,512
[45] Dec. 30, 1980

[54] NOVEL THIOAMIDE DERIVATIVES CONTAINING A PYRIDAZINE GROUP

[75] Inventors: Masahiro Takaya; Toshihiro Yamada, both of Shiga; Tomokazu Yuizono, Kyoto, all of Japan

[73] Assignee: Morishita Pharmaceutical Co., Ltd., Japan

[21] Appl. No.: 63,869

[22] Filed: Aug. 6, 1979

Related U.S. Application Data

[63] Continuation-in-part of Ser. No. 872,367, Jan. 26, 1978, abandoned.

[51] Int. Cl.³ .................. C07D 237/08; C07D 237/14; C07D 237/18; A61K 31/50
[52] U.S. Cl. ..................................... 544/239; 424/250; 544/224
[58] Field of Search ......................................... 544/239

[56] References Cited

U.S. PATENT DOCUMENTS

| | | | |
|---|---|---|---|
| 3,624,085 | 11/1971 | Malen et al. | 260/294.8 E |
| 3,657,243 | 4/1972 | Quintilla | 260/250 A |
| 3,686,190 | 8/1972 | Malen et al. | 260/294.8 E |
| 3,825,547 | 7/1974 | Loev | 260/250 A |

*Primary Examiner*—Mark L. Berch
*Attorney, Agent, or Firm*—McGlew and Tuttle

[57] ABSTRACT

Novel pyridazine-containing thioamide derivatives of the formula

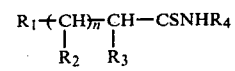

wherein $R_1$ is

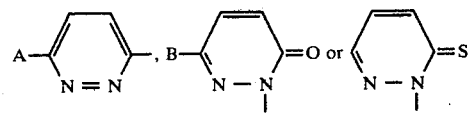

wherein A is hydrogen, methyl, phenyl or mercapto, and B is hydrogen or phenyl; $R_2$ is hydrogen or methyl; $R_3$ is hydrogen, methyl or phenyl; $R_4$ is hydrogen or methyl; and n is zero or 1. The derivatives have outstanding gastric antisecretory activity.

7 Claims, No Drawings

NOVEL THIOAMIDE DERIVATIVES CONTAINING A PYRIDAZINE GROUP

CROSS REFERENCE TO RELATED APPLICATION

This application is a continuation-in-part of U.S. Ser. No. 872,367 filed Jan. 26, 1978 and is copending therewith, now abandoned.

BACKGROUND OF THE INVENTION

1. Field of the Invention

This invention relates to novel pyridazine-containing thioamide derivatives having high gastric anti-secretory activity and represented by the formula:

$$R_1 + CH +_n CH - CSNHR_4 \qquad (I)$$
$$\phantom{R_1 + CH +_n} | \quad |$$
$$\phantom{R_1 + CH +_n} R_2 \quad R_3$$

wherein $R_1$ is a group having a pyridazine skeleton with or without a substituent, $R_2$ is hydrogen or methyl, $R_3$ is hydrogen, methyl or phenyl, $R_4$ is hydrogen or methyl, and n is zero or 1. The group $R_1$ is represented by

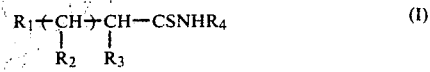

wherein A is hydrogen, methyl, phenyl or mercapto, and B is hydrogen or phenyl.

2. The Prior Art

As is well known, G. D. Searle & Co. in 1967 developed 2-phenyl-2-(2-pyridyl)thioacetamide (SC-15396) as an antigastrin agent having anti-ulcer activity (D. L. Cook, R. G. Bianchi, Life Sci., 6 1381, 1964). Concurrently various analogous compounds were developed (R. G. Bianchi, D. L. Cook, Federation Proc., 27, 1331, 1968; Belg., 669,165 (1966); Ger. Offen., 1,934,392 (1970); Ger. Offen. No. 2,188,331 (1972); U.S. Pat. No. 3,624,085; 3,686,190).

Along with the synthesis of such active compounds, advanced research was conducted on the correlation between gastric antisecretory effects and chemical structural formulae, leading to the conclusion that thioacetamide is of significance as a group for producing the desired activity (C. E. Malen, B. H. Danree, X. B. L. Pascaud, J. Med. Chem., 14 (13), 244, 1971; J. M. Bustard Y. C. Martin, J. Med. Chem., 15 (11), 1101 1972). Directing attention to the reduced side effects and remarkably sustained activity of thioamide derivatives containing a pyridazine skeleton, we carried out research on the synthesis of such thioamide derivatives despite the difficulties encountered in the preparation thereof and the complexity of the process required. Our efforts have resulted in this invention.

The pyridazine-containing thioamide derivatives of this invention represented by the formula (I) are prepared from nitrile derivatives or acid amide derivatives, which are obtained by the following methods. (1) Nitrilepyridazine derivatives (II) are synthesized by preparing a 3-halogenopyridazine derivative according to the method disclosed in A. Staehelin, K. Eichenberger, J. Druey, Helv. Chem. Acta., 39, 1741, 1956 and reacting benzylcyanide with the derivative as represented by the following equation in the process of sodium amide.

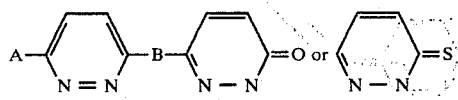

II-1: A = H
II-2: A = CH₃
II-3: A = C₆H₅
II-4: A = Cl (2) Although it is known to synthesize 2-pyridazinyl alkylcyanide by Hensell's method (H. P. Hensell, H. Bauman, B.P. 946,471 (1961) or Feuer's method (J. Feuer, J. Am. Chem. Soc., 80, 5877, 1958), we have found a novel method of synthesizing nitrile derivatives (III) or acid amide derivatives (IV) by reacting an acrylonitrile derivative or acrylamide derivative with a 6-suubstituted-3-oxo-(2H)pyridazine as expressed by the following equation in the presence of a catalytic amount of Triton-B (trimethyl benzylammonium hydroxide, 40% methanol solution).

III-1: B = R₂ = R₃ = H
III-2: B = C₆H₅, R₂ = R₃ = H
III-3: B = R₂ = H, R₃ = CH₃

IV-1: B = R₂ = R₃ = H, R₄ = CH₃
IV-2: B = R₃ = H, R₂ = R₄ = CH₃

(3) Compounds (V) having lactumthicketone are synthesized by reacting a 3-oxo-2-pyridazinylalkylnitrile with phosphorous pentasulfide as represented by the following equation.

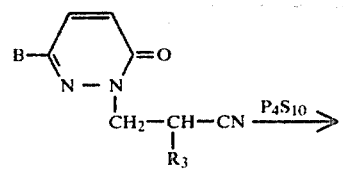

$P_4S_{10}$

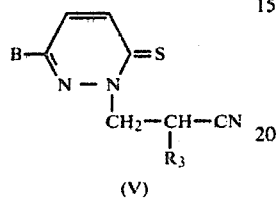

(V)

V-1: $B = R_3 = H$
V-2: $B = H, R_3 = CH_3$

The compounds (I) according to this invention are prepared from the starting materials described above by the following processes.

(1) 6-Substituted-3-pyridazinylthioacetamides (IA) are prepared by reacting hydrogen sulfide with a nitrile derivative (II) as dissolved in pyridine in the presence of pyrrolidine or triethylamine serving as a catalyst.

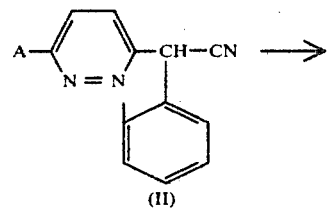

IA-1: $A = H$
IA-2: $A = CH_3$
IA-3: $A = C_6H_5$
IA-4: $A = SH$

However, 2-phenyl-2-(6-mercapto-3-pyridazinyl)-thioacetamide is prepared from 2-phenyl-2-(6-chloro-3-pyridazinyl)acetonitrile.

(2) 2-Pyridazinyl-alkylthioacetamides (IB) are prepared by reacting a nitrile derivative (III) or an acid amide derivative (IV) with phosphorus pentasulfide in pyridine.

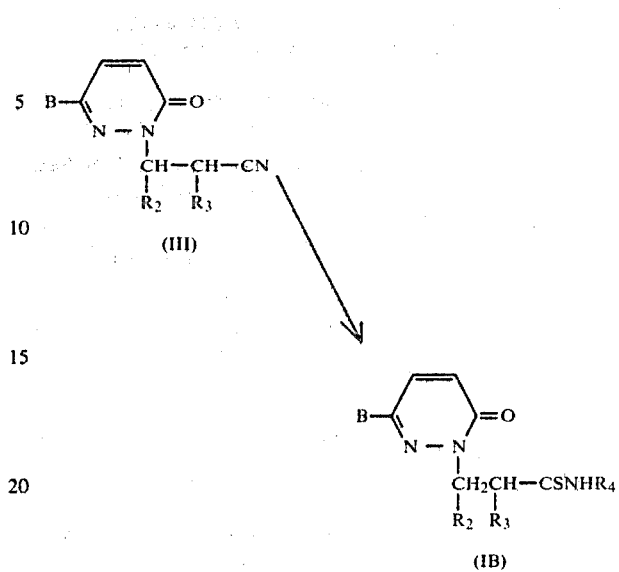

IB-1: $B = R_2 = R_3 = R_4 = H$
IB-2: $B = C_6H_5, R_2 = R_3 = R_4 = H$
IB-3: $B = R_2 = R_3 = H, R_4 = CH_3$
IB-4: $B = R_3 = H, R_2 = R_4 = CH_3$ (3) 3-Thio-2-pyridazinyl-alkylthioacetamides (IC) are prepared by reacting hydrogen sulfide with a nitrile derivative (V) as dissolved in pyridine in the presence of pyrrolidine or triethylamine serving as a catalyst.

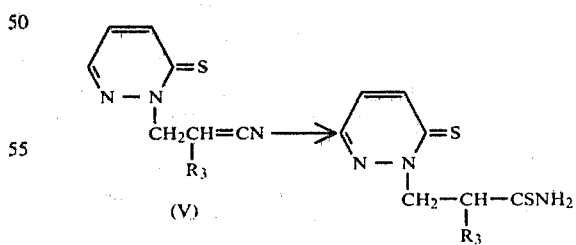

IC-1: $R_3 = H$
IC-2: $R_3 = H$

The compounds (I) of this invention prepared by the foregoing processes include those listed in Table I below.

TABLE 1

$$R_1 \!-\!(CH\!-\!)_{\overline{n}}\, CH\!-\!CSNHR_4$$
$$\phantom{R_1\!-\!(CH\!-\!)_{\overline{n}}}\, |\phantom{xxxx}| $$
$$\phantom{R_1\!-\!(CH\!-\!)_{\overline{n}}}\, R_2\phantom{xx}R_3$$

| Compound No. | $R_1$ | $R_2$ | $R_3$ | $R_4$ | n |
|---|---|---|---|---|---|
| IA-1 | 3-pyridazinyl | — | $C_6H_5$ | H | 0 |
| IA-2 | 6-methyl-3-pyridazinyl | — | $C_6H_5$ | H | 0 |
| IA-3 | 6-phenyl-3-pyridazinyl | — | $C_6H_5$ | H | 0 |
| IA-4 | 6-mercapto-3-pyridazinyl | — | $C_6H_5$ | H | 0 |
| IB-1 | 6-oxo-1,6-dihydropyridazin-3-yl | H | H | H | 1 |
| IB-2 | 4-phenyl-6-oxo-1,6-dihydropyridazin-3-yl | H | H | H | 1 |
| IB-3 | 6-oxo-1,6-dihydropyridazin-3-yl | H | H | $CH_3$ | 1 |
| IB-4 | 6-oxo-1,6-dihydropyridazin-3-yl | $CH_3$ | H | $CH_3$ | 1 |
| IC-1 | 6-thioxo-1,6-dihydropyridazin-3-yl | H | H | H | 1 |
| IC-2 | 6-thioxo-1,6-dihydropyridazin-3-yl | H | $CH_3$ | H | 1 |

Most of the compounds of formula (I) were found to have an excellent gastric antisecretory activity, which was evaluated in the 4 hours pylorus ligated rate according to Shay's method (H. Shay, D. C. H. Sun and M. Gruenstein, Gastroenterology, 21 906, 1954).

This invention will be described below in greater detail with reference to examples, in which the desired compounds prepared are referred to by the corresponding numbers given in Table 1 above.

EXAMPLE 1

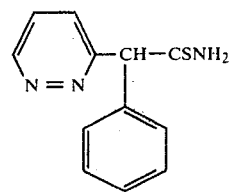

2-Phenyl-2-(3-pyridazinyl)thioacetamide (IA-1)

A 1.0 g quantity (0.005 mols) of 2-phenyl-2-(3-pyridazinyl)acetonitrile was dissolved in 50 ml of dry pyridine in a sealed tube, and 4 ml of triethylamine was added. After allowing the resulting solution to stand for 1.5 hours, dry hydrogen sulfide was passed through the solution in a steady stream at room temperature for 15 minutes. The sealed mixture was then left to stand at room temperature for 24 hours. The reaction mixture was concentrated in a vacuum to give a yellow solid cake. Recrystallization of the concentrate from ethanol afforded 1.1 g (94% yield) of 2-phenyl-2-(3-pyridazinyl)thioacetamide in the form of pale yellow plates, m.p. 161° to 163° C.

| | Elementary analysis | | |
|---|---|---|---|
| | C (%) | H (%) | N (%) |
| Calcd. for $C_{12}H_{11}N_3S$ | 62.86 | 4.84 | 18.33 |
| Found: | 62.67 | 4.82 | 18.63 |

Infrared spectrum (KBr) cm$^{-1}$: 2260, 3120 (NH$_2$).

The starting material, 2-phenyl-2-(3-pyridazinyl)-acetonitrile, was prepared in the following manner.

To a stirred solution of 6 g. (0.05 mole) of 3-chloropyridazine and 5.2 g (0.06 mole) of phenylacetonitrile in 100 ml of dry benzene was added 1.6 g (0.06 mole) of pulverized sodium amide on a water-ice bath. The mixture was allowed to stand for several hours at room temperature and refluxed for four hours. After cooling, the mixture was neutralized with 10% hydrochloric acid and extracted with benzene. The benzene phase was washed with water, dried over anhydrous sodium sulfate and concentrated in vacuo to give a red-orange oil. The oil was crystallized from a mixture of ethanol and isopropyl ether to give 3.9 g (38%) of pale red needles, m.p. 136° to 137° C.

| | Elementary analysis | | |
|---|---|---|---|
| Calcd. for $C_{12}H_9N_3$: | 73.83 | 4.65 | 21.53 |
| Found: | 74.05 | 4.69 | 21.53 |

Infrared spectrum (KBr) cm$^{-1}$: 2260 (CN).

EXAMPLE 2

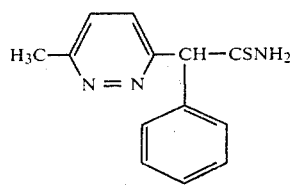

2-Phenyl-(6-methyl-3-pyridazinyl)thioacetomide (IA-2)

A 2.0 g quantity (0.01 mole) of 2-phenyl-2-(6-methyl-3-pyridazinyl)acetonitrile was dissolved in 60 ml of dry pyridine in a sealed tube, and 15 ml of triethylamine was added. After allowing the solution to stand for 1.5 hours, dry hydrogen sulfide was passed through the solution in a steady stream at 0° C. for 10 to 15 minutes. The sealed mixture was then allowed to stand at room temperature for three days. The reaction mixture was concentrated in a vacuum, the residue dissolved in chloroform, and the solution shaken with water. This extraction procedure was repeated several times. The combined extract was dried over anhydrous sodium sulfonate, shaken with Norit, filtered, and the filtrate was distilled. The residue was recrystallized from a mixture of acetonitrile and isopropyl ether, giving 1.6 g (66.7% yield) of yellow powder, m.p. 132°–135° C.

| | Elementary Analysis | | |
|---|---|---|---|
| | C (%) | H (%) | N (%) |
| Calcd. for $C_{13}H_{13}N_3S$: | 64.17 | 5.39 | 17.27 |
| Found: | 64.21 | 5.37 | 17.41 |

Infrared spectrum (KBr) cm$^{-1}$: 3280, 3150 (NH$_2$).

The starting material was prepared by the following procedure.

To a solution of 6.5 g (0.05 mole) of 3-chloro-6-methylpyridazine and 7.0 g (0.06 mole) of phenylacetonitrile in 50 ml of dry benzene was gradually added 4.0 g of pulverized sodium amide. The mixture was then slowly heated to 80° to 90° C. and maintained at this temperature for one hour. The reaction mixture was thereafter treated in the same manner as in the preparation of 2-phenyl-2-(3-pyridazinyl)-acetonitrile (see Example 1). The resulting product was recrystallized from a mixture of ethanol and isopropyl ether, giving 6.0 g (58% yield) of 2-phenyl-2-(6-methyl-3-pyridazinyl acetonitrile as pale yellow crystals, m.p. 121°–122° C. (decomp.).

| | Elementary analysis | | |
|---|---|---|---|
| | C (%) | H (%) | N (%) |
| Calcd. for $C_{13}H_{11}N_3$: | 74.41 | 5.09 | 19.97 |
| Found: | 74.62 | 5.30 | 20.08 |

Infrared spectrum (KBr) cm$^{-1}$: 2250 (CN).

EXAMPLE 3

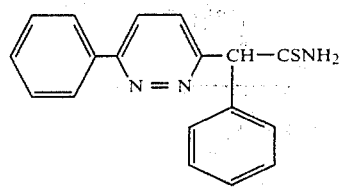

2-Phenyl-2-(6-phenyl-3-pyridazinyl)thioacetamide (IA-3)

Following the same procedure as in Example 2, 1.0 g (48% yield) of 2-phenyl-2-(6-phenyl-3-pyridazinyl)-thioacetamide was prepared from 2.12 g (0.008 mole) of 2-phenyl-2-(6-phenyl-3-pyridazinyl)acetonitrile and dry hydrogen sulfide. The desired pure product was obtained by recrystallization from acetonitrile and isopropyl ether, m.p. 135°–139° C.

| | Elementary Analysis | | |
|---|---|---|---|
| | C (%) | H (%) | N (%) |
| Calcd. for $C_{18}H_{15}N_3S$: | 70.79 | 4.95 | 13.76 |
| Found: | 70.89 | 4.74 | 14.01 |

Infrared spectrum (KBr) cm$^{-1}$: 3280, 3150 (NH$_2$).

The starting material was prepared by the following procedure.

To a solution of 5.7 g. (0.03 mole) of 3-chloro-6-phenylpyridazinone and 4.1 g (0.035 mole) of phenylacetonitrile in 50 ml of dry benzene was gradually added 7.8 g (0.07 mole) of pulverized sodium amide. The mixture was slowly heated to 80° to 90° C. and maintained at this temperature for one hour. The resulting precipitate was filtered off, thoroughly washed with benzene and water, giving 4.8 g (59% yield) of 2-phenyl-2-(6-phenyl-3-pyridazinyl)acetonitrile in the form of pale yellow crystals, m.p. 201°–203° C. (decomp.).

| | Elementary analysis | | |
|---|---|---|---|
| | C (%) | H (%) | N (%) |
| Calcd. for $C_{18}H_{13}N_3$: | 79.68 | 4.83 | 15.47 |
| Found: | 79.47 | 4.83 | 15.30 |

Infrared spectrum (KBr) cm$^{-1}$: 2250 (CN).

EXAMPLE 4

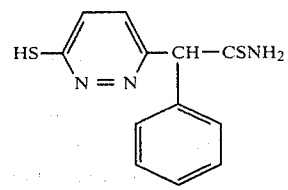

2-Phenyl-2-(6-mercapto-3-pyridazinyl)thioacetamide (IA-4)

In the same manner as in Example 1, 2-phenyl-2-(6-mercapto-3-pyridazinyl)thioacetamide was prepared from 1.5 g (0.066 mole) of 2-phenyl-2-(6-chloro-3- pyridazinyl)-acetonitrile and dry hydrogen sulfide. The purified product, 1.1 g (65% yield), was a yellow powder, m.p. 192°–193° C. (decomp.).

| | Elementary analysis | | |
|---|---|---|---|
| | C (%) | H (%) | N (%) |
| Calcd. for $C_{12}H_{11}N_3S$: | 55.15 | 4.24 | 16.08 |
| Found: | 55.03 | 4.36 | 16.14 |

Infrared spectrum (KBr) cm$^{-1}$: 3420, 3280 (NH$_2$).

The starting material was prepared by the following procedure.

To a solution of 8.2 g (0.07 mole) of phenylacetonitrile in 50 ml of dry tetrahydrofuran was added 1.61 g (0.07 mole) of pulverized lithium amide. The mixture was refluxed for 5 hours. To the reaction mixture thereafter cooled were added 8.2 g (0.055 mole) of 3,6-dichloropyridazine and 10 ml of tetrahydrofuran on a water-ice bath. The mixture was then allowed to stand overnight at room temperature. The resulting mixture was neutralized and then distilled to remove the tetrahydrofuran. The residue was chromatographed over silica gel, followed by recrystallization from a mixture of ethanol and isopropyl ether, giving 5.4 g (42.9% yield) of 2-phenyl-2-(6-chloro-3-pyridazinyl)acetonitrile in the form of pale red needles, m.p. 131° C.

| | Elementary analysis | | |
|---|---|---|---|
| | C (%) | H (%) | N (%) |
| Calcd. for $C_{12}H_8ClN_3$: | 62.76 | 3.51 | 18.30 |
| Found: | 62.49 | 3.63 | 18.24 |

Infrared spectrum (KBr) cm$^{-1}$: 2250 (CN).

EXAMPLE 5

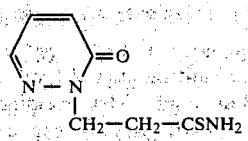

3-(3-Oxo-2-pyridazinyl)thiopropionamide (IB-1)

A mixture of 1.49 g (0.01 mole of 3-(3-oxo-2-pyridazinyl)propionitrile, 10 ml of triethylamine and 40 ml of dry pyridine was stirred in a sealed tube at room temperature for one hour. Subsequently dry hydrogen sulfide was passed through the mixture in a steady stream for 15 minutes. The sealed mixture was then stirred at room temperature for 1 day. The solvent was removed in a vacuum to afford a yellow crystalline residue, which was then recrystallized from ethanol and isopropyl ether, giving 1.7 g (93% yield) of white crystals, m.p. 145°–147° C.

| | Elementary analysis | | |
|---|---|---|---|
| | C (%) | H (%) | N (%) |
| Calcd. for $C_7H_9N_3OS$: | 45.89 | 4.94 | 22.94 |
| Found: | 45.89 | 4.81 | 22.93 |

Infrared spectrum (KBr) cm$^{-1}$: 3250, 3100 (NH$_2$).

The starting material was prepared by the following procedure.

To a stirred solution of 3.84 g (0.04 mole) of 3(2H)-pyridazinone, 2.33 g (0.044 mole) of acrylonitrile in 50 ml of ethanol, 1 ml of Triton-B (trimethyl benzylammonium hydroxide, 40% methanol solution) was added dropwise. The mixture was stirred for 2 hours at 60° C. and then evaporated to dryness in a vacuum on a steam bath, giving a dark orange oil. The oil was dissolved in ethanol, shaken with Norit and filtered. The filtrate was distilled. Recrystallization of the residue from ethanol and isopropyl ether gave 4.7 g (79% yield) of 3-(3-oxo-2-pyridazinyl)-propionitrile in the form of pale yellow crystals, m.p. 75°–76° C.

| | Elementary analysis | | |
|---|---|---|---|
| | C (%) | H (%) | N (%) |
| Calcd. for $C_7H_7N_3O$: | 56.37 | 4.73 | 28.18 |
| Found: | 56.41 | 4.86 | 28.22 |

Infrared spectrum (KBr) cm$^{-1}$: 2260 (CN).

EXAMPLE 6

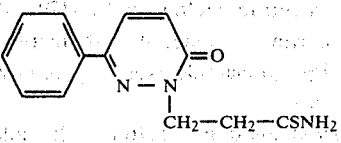

3-(3-Oxo-6-phenyl-2-pyridazinyl)thiopropionamide (IB-2)

3-(3-Oxo-6-phenyl-2-pyridazinyl)thiopropionamide was synthesized from 3-(3-oxo-6-phenyl-2-pyridazinyl)-propionitrile in the same manner as in Example 5, m.p. 173°–175° C. (85% yield).

| | Elementary analysis | | |
|---|---|---|---|
| | C (%) | H (%) | N (%) |
| Calcd. for $C_{13}H_{11}N_3OS$: | 60.21 | 5.05 | 16.20 |
| Found: | 60.31 | 5.01 | 16.39 |

Infrared spectrum (KBr) cm$^{-1}$: 3250, 3080 (NH$_2$).

3-(3-Oxo-6-phenyl-2-pyridazinyl)propionitrile was prepared from 6-phenyl-3(2H)-pyridazinone in the same manner as in the preparation of the starting material of Example 1, m.p. 103°–104° C. (79% yield).

| | Elementary analysis | | |
|---|---|---|---|
| | C (%) | H (%) | N (%) |
| Calcd. for $C_{13}H_{11}N_3O$: | 69.32 | 4.92 | 18.66 |
| Found: | 69.39 | 4.71 | 18.69 |

Infrared spectrum (KBr) cm$^{-1}$: 2250 (CN).

EXAMPLE 7

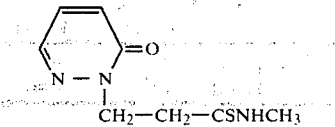

N-Methyl-3-(3-Oxo-2-pyridazinyl)thiopropionamide (IB-3)

A mixture of 3 g (0.017 mole) of N-methyl-3-(3-oxo-2-pyridazinyl)propionamide and 3.55 g of phosphorus pentasulfide in dry pyridine (50 ml) was heated at 120° C. for 15 minutes. The reaction mixture was concentrated at reduced pressure, and the concentrate was diluted with 20 ml of 10% sodium hydroxide solution and extracted with chloroform. After the solvent was evaporated off, the residue was recrystallized from chloroform and isopropyl ether to give 1.6 g (49% yield) of yellow prisms, m.p. 142°–144° C.

| | Elementary analysis | | |
|---|---|---|---|
| | C (%) | H (%) | N (%) |
| Calcd. for $C_8H_{11}N_3OS$: | 48.71 | 5.62 | 21.30 |
| Found: | 48.64 | 5.66 | 21.38 |

Infrared spectrum (KBr) cm$^{-1}$: 3270, 3100 (NH).

The starting material, N-methyl-3-(3-oxo-2-pyridazinyl)propionamide, was prepared by the following procedure.

To a stirred solution of 5.76 g (0.06 mole) of 3(2H)-pyridazinone and 8 g (0.08 mole) of ethyl acrylate in 100 ml of ethanol, 2 ml of Triton-B was added dropwise while maintaining the temperature at 0° C. The mixture was refluxed for 4 hours, then distilled to give an orange oil residue. The crude oil was extracted with chloroform. The extract was washed with water, dried over anhydrous sodium sulfate and distilled. The residual oil was distilled in a vacuum to give 9.7 g (83% yield) of ethyl-3-(3-oxo-2-pyridazinyl)propionate as a colorless liquid boiling at 120°/121° C./1 mm Hg.

| | Elementary analysis | | |
|---|---|---|---|
| | C (%) | H (%) | N (%) |
| Calcd. for $C_9H_{12}O_3N_2 \cdot \frac{1}{2}H_2O$ | 53.45 | 6.31 | 13.85 |
| Found | 53.16 | 6.18 | 13.95 |

Infrared spectrum (KBr) cm$^{-1}$: 1740 (COO), 1670 (CO).

Next a mixture of 1.96 g (0.01 mole) of ethyl-3-(3-oxo-2-pyridazinyl)propionate and 20 ml of methylamine (30% ethanol solution was stirred at 40° C. for 30 hours and distilled to give white crystals. Recrystallization from ethanol gave 1.6 g (82% yield of N-methyl-3-(3-oxo-2-pyridazinyl)propionamide, m.p. 94°–96° C.

| | Elementary analysis | | |
|---|---|---|---|
| | C (%) | H (%) | N (%) |
| Calcd. for $C_8H_{11}O_2N_3$: | 53.03 | 6.12 | 23.19 |
| Found: | 52.90 | 5.94 | 22.97 |

Infrared spectrum (KBr) cm$^{-1}$: 2950 ($CONH_2$).

EXAMPLE 8

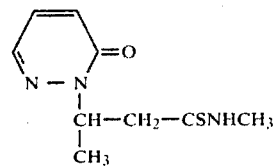

N-Methyl-3-methyl-3-(3-oxo-2-pyridazinyl)thiopropionamide (IB-4).

A solution of 3.6 g of N-methyl-3-methyl-3-(3-oxo-2-pyridazinyl)propionamide and 4.44 g of phosphorus pentasulfide in 50 ml of dry pyridine was heated at 120° C. for 15 minutes. The same procedure as in Example 7 was thereafter repeated to give a purified product, m.p. 155°–157° C. (2.0 g, 52% yield).

| | Elementary analysis | | |
|---|---|---|---|
| | C (%) | H (%) | N (%) |
| Calcd. for $C_9H_{13}N_3OS$: | 51.16 | 6.20 | 19.89 |
| Found: | 51.23 | 6.01 | 20.10 |

Infrared spectrum (KBr) cm$^{-1}$: 3260, 3080 (NH).

EXAMPLE 9

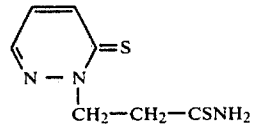

3-(3-Thio-2-pyridazinyl)thiopropionamide (IC-1)

A 2.1 g quantity (0.0127 mole) of 3-(3-thio-2-pyridazinyl)propionitrile and 10 ml of triethylamine were dissolved in 40 ml of dry pyridine. After the solution was saturated with dry hydrogen sulfide, the mixture was left to stand in a sealed tube at room temperature for 48 hours. The reaction mixture was concentrated in a vacuum to give crude yellow crystals. Recrystallization of the product from chloroform gave 2.4 g (95% yield) of pale yellow prisms, m.p. 163°–163° C.

| | Elementary analysis | | |
|---|---|---|---|
| | C (%) | H (%) | N (%) |
| Calcd. for $C_7H_9N_3S_2$: | 42.19 | 4.55 | 21.08 |
| Found: | 42.24 | 4.51 | 22.16 |

Infrared spectrum (KBr) cm$^{-1}$: 3280, 3180 ($NH_2$).

The starting material was prepared in the following manner.

To a solution of 3 g (0.02 mole) of 3-(3-oxo-2-pyridazinyl)propionitrile in 50 ml of dry pyridine, 4.4 g (0.02 mole) of phosphorus pentasulfide was added. The mixture was heated at 120° C. for 3 hours and distilled. The residue was dissolved in 10% sodium hydroxide solution and extracted with chloroform. The chloroform phase was then extracted with 10% hydrochloric acid solution. The solution was thereafter neutralized with 10% aqueous solution of sodium carbonate. The neutral solution was further extracted with chloroform. The extract was washed with water, dried and distilled, giving a yellow solid cake. Recrystallization of the product from ethanol gave 2.7 g of 3-(3-thio-2-pyridazinyl) propionitrile in the form of yellow prisms, m.p. 63°–64° C.

| Elementary analysis | | | |
|---|---|---|---|
| | C (%) | H (%) | N (%) |
| Calcd. for $C_7H_7N_3S$: | 50.91 | 4.27 | 25.45 |
| Found: | 51.00 | 4.30 | 25.60 |

Infrared spectrum (KBr) $cm^{-1}$: 2250 (CN), 1080 (C=S).

EXAMPLE 10

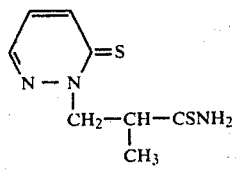

2-Methyl-3-(3-thio-2-pyridazinyl)thiopropionamide (IC-2)

This compound was prepared from 2-methyl-3-(3-thio-2-pyridazinyl)propionitrile in the same manner as in Example 9, m.p. 108°–109° C. (60% yield).

| Elementary analysis | | | |
|---|---|---|---|
| | C (%) | H (%) | N (%) |
| Calcd. for $C_8H_{11}N_3S_2$: | 45.04 | 5.20 | 19.95 |
| Found: | 45.13 | 5.20 | 19.95 |

Infrared spectrum (KBr) $cm^{-1}$: 3260, 3110 ($NH_2$).

The starting material, 2-methyl-3-(3-thio-2-pyridazinyl)propionitrile was prepared from 2-methyl-3-(3-oxo-2-pyridazinyl)propionitrile by the same method as in the preparation of the starting material of Example 9, m.p. 82°–83° C, (67% yield).

| Elementary analysis | | | |
|---|---|---|---|
| | C (%) | H (%) | N (%) |
| Calcd. for $C_8H_9N_3S$: | 53.62 | 5.06 | 23.45 |
| Found: | 53.75 | 5.20 | 23.55 |

Infrared spectrum (KBr) $cm^{-1}$: 2230 (CN), 1090 (C=S).

EXAMPLE 11

As illustrative evidence of the remarkable high gastric antisecretory activity of the compounds of the invention, tests were conducted on, and comparisons made with, closely similar compounds in the prior art. The following Tables 2 and 3 show the results of such tests according to previously identified techniques from the literature. These results show a great difference in activity without overlapping or touching of ranges for the data found.

TABLE 2

Effect on aspirin-induced gastric ulcers in pylorus-ligated rats and acute toxicity in mice.

| Compound | Dose mg/kg | No. of Rats | Inhibition (%) | $ED_{50}$ (mg/kg) | 50 (mg/kg) P.O. Orally | Safety Margin $LD_{50}/ED_{50}$ |
|---|---|---|---|---|---|---|
| (Ex. 1) | 10 | 10 | 48.6 | 11.5 | 980 | 85.12 |
| | 30 | 10 | 97.7 | | | |
| (Ex. 2) | 10 | 10 | 3.2 | 21.0 | 1700 | 80.95 |
| | 30 | 10 | 89.0 | | | |
| (U.S. Pat. No. 3,624,085 Ex. 9) | 10 | 10 | 22.3 | 18.5 | 1200 | 64.86 |
| | 30 | 10 | 74.0 | | | |

TABLE 2-continued
Effect on aspirin-induced gastric ulcers in pylorus-ligated rats and acute toxicity in mice.

| Compound | Dose mg/kg | No. of Rats | Inhibition (%) | ED$_{50}$ (mg/kg) | LD$_{50}$ (mg/kg) P.O. Orally | Safety Margin LD$_{50}$/ED$_{50}$ |
|---|---|---|---|---|---|---|
| 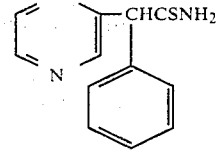 (U.S. Pat. No. 3,624,085 Ex. 12) | 10<br>30 | 10<br>10 | 15.4<br>50.8 | 30.0 | 924 | 30.80 |
| 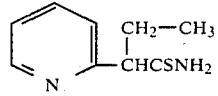 (U.S. Pat. No. 3,686,190 Ex. 1) | 10<br>30 | 10<br>10 | 11.3<br>45.7 | 52.0 | 670 | 12.88 |
| Control (CMC) | | 20 | 0 | | | |

NOTE:
Each drug was given eight intraduodenally (i.d.) immediately after pylorus ligation in a volume of 0.5 ml/100 g of body weight. Animals were sacrificed 7 hrs after aspirin (100 mg/kg, p.o.) administration.

TABLE 3
Effect on Shay ulceration in rats and acute toxicity in mice.

| Compound | Dose (mg/kg) | No. of Rats | Inhibition (%) | ED$_{50}$ (mg/kg) | LD$_{50}$ (mg/kg) P.O. (orally) | Safety Margin LD$_{50}$/ED$_{50}$ |
|---|---|---|---|---|---|---|
| 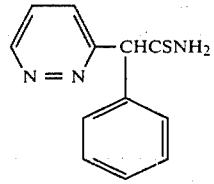 (Ex. 1) | 10<br>30 | 10<br>10 | 33.3<br>95.8 | 12.5 | 980 | 78.40 |
| 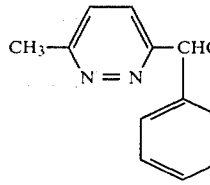 (Ex. 2) | 10<br>30 | 10<br>10 | 50.0<br>91.7 | 11.0 | 1700 | 154.54 |
| 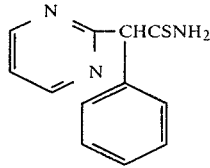 (U.S. Pat. No. 3,624,085 Ex. 9) | 10<br>30 | 10<br>10 | 28.2<br>65.0 | 26.0 | 1200 | 46.15 |
| 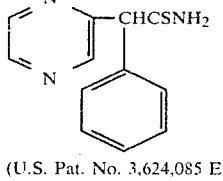 (U.S. Pat. No. 3,624,085 Ex. 12) | 10<br>30 | 10<br>10 | 18.3<br>57.7 | 28.0 | 924 | 33.00 |
| 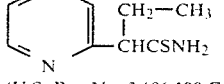 (U.S. Pat. No. 3,686,190 Ex. 1) | 10<br>30 | 10<br>10 | 12.0<br>46.5 | 34.0 | 670 | 17.70 |

TABLE 3-continued

| | | | | | LD$_{50}$ | Safety |
| Compound | Dose (mg/kg) | No. of Rats | Inhibition (%) | ED$_{50}$ (mg/kg) | (mg/kg) P.O. (orally) | Margin LD$_{50}$/ED$_{50}$ |
| --- | --- | --- | --- | --- | --- | --- |
| Control (CMC) | | 20 | 0 | | | |

Note:
Each drug was given either intraduodenally (i.d.) immediately after pylorus ligation in a volume of 0.5 ml/100 g of body weight. The animals were sacrificed 13 hours after drug treatment.

What is claimed is:

1. A thioamide having the formula

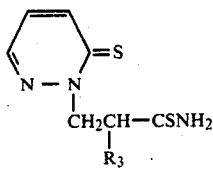

wherein $R_3$ is hydrogen or methyl.

2. A thioamide as claimed in claim 1, which is 3-(3-thio-2-pyridazinyl)thiopropionamide.

3. A thioamide as claimed in claim 1, which is 2-methyl-3-(3-thio-2-pyridazinyl)thiopropionamide.

4. 3-(3-oxo-2-pyridazinyl) thiopropionamide.

5. 3-(3-oxo-6-phenyl-2-pyridazinyl) thiopropionamide.

6. N-methyl-3-(3-oxo-2-pyridazinyl) thiopropionamide.

7. N-methyl-3-methyl-3-(3-oxo-2-pyridazinyl) thiopropionamide.

* * * * *